(12) United States Patent
Blasco et al.

(10) Patent No.: US 7,071,334 B2
(45) Date of Patent: Jul. 4, 2006

(54) 6-(2-CHLORO-6-FLUORO-PHENYL)-TRIAZOLOPYRIMIDINES

(75) Inventors: Jordi Tormo i Blasco, Limburgerhof (DE); Hubert Sauter, Mannheim (DE); Bernd Müller, Frankenthal (DE); Markus Gewehr, Kastellaun (DE); Wassilios Grammenos, Ludwigshafen (DE); Thomas Grote, Wachenheim (DE); Andreas Gypser, Mannheim (DE); Joachim Rheinheimer, Ludwigshafen (DE); Ingo Rose, Mannheim (DE); Peter Schäfer, Ottersheim (DE); Frank Schieweck, Hessheim (DE); Eberhard Ammermann, Heppenheim (DE); Siegfried Strathmann, Limburgerhof (DE); Gisela Lorenz, Hambach (DE); Reinhard Stierl, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 218 days.

(21) Appl. No.: 10/474,461

(22) PCT Filed: Apr. 6, 2002

(86) PCT No.: PCT/EP02/03830

§ 371 (c)(1),
(2), (4) Date: Oct. 8, 2003

(87) PCT Pub. No.: WO02/083677

PCT Pub. Date: Oct. 24, 2002

(65) Prior Publication Data

US 2004/0110751 A1   Jun. 10, 2004

(30) Foreign Application Priority Data

Apr. 11, 2001 (EP) .................. 01 109010

(51) Int. Cl.
C07D 487/04 (2006.01)
A01N 43/90 (2006.01)
(52) U.S. Cl. .................. 544/263; 514/259.31
(58) Field of Classification Search ........... 514/259.31; 544/263
See application file for complete search history.

(56) References Cited

U.S. PATENT DOCUMENTS

| 4,567,263 A | 1/1986 | Eicken et al. ........ 544/263 |
| 5,994,360 A | 11/1999 | Pfrengle ............ 514/259.31 |
| 2002/0068744 A1* | 6/2002 | Schmitt et al. ....... 514/259.31 |

FOREIGN PATENT DOCUMENTS

| EP | 550 113 | 7/1993 |
| FR | 2 784991 | 4/2000 |
| WO | 98/46607 | 10/1998 |
| WO | 99/41255 | 8/1999 |

* cited by examiner

*Primary Examiner*—Thomas C. McKenzie
(74) *Attorney, Agent, or Firm*—Novak Druce & Quigg, LLP; Jason D. Voight

(57) ABSTRACT

6-(2-Chloro-6-fluoro-phenyl)-triazolopyrimidines of formula (I), in which $R^1$ and $R^2$ independently denote hydrogen or alkyl, alkenyl, alkynyl, alkadienyl, or haloalkyl, cycloalkyl, bicycloalkyl, phenyl, naphthyl, or 5- or 6-membered heterocyclyl, containing one to four nitrogen atoms or one to three nitrogen atoms and one sulfur or oxygen atom, or 5- or 6-membered heteroaryl, containing one to four nitrogen atoms or one to three nitrogen atoms and one sulfur or oxygen atom, or where $R^1$ and $R^2$ radicals may be unsubstituted or partially or fully halogenated or may be substituted as defined in the description. $R^1$ and $R^2$ together with the interjacent nitrogen atom represent a 5- or 6-membered heterocyclic ring, containing one to four nitrogen atoms or one to three nitrogen atoms and one sulfur or oxygen atom, which may be substituted; X is cyano, alkoxy, haloalkoxy or alkenyloxy; processes for their preparation, compositions containing them and to their use for combating phytopathogenic fungi (I)

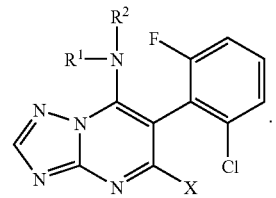

13 Claims, No Drawings

6-(2-CHLORO-6-FLUORO-PHENYL)-TRIAZOLOPYRIMIDINES

The invention relates to 6-(2-chloro-6-fluoro-phenyl)-triazolopyrimidines of formula I

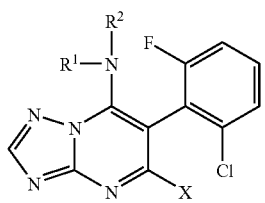

in which
- $R^1$ and $R^2$ independently denote hydrogen or
  $C_1$–$C_{10}$-alkyl, $C_2$–$C_{10}$-alkenyl, $C_2$–$C_{10}$-alkynyl, $C_4$–$C_{10}$-alkadienyl, or $C_1$–$C_{10}$-haloalkyl,
  $C_3$–$C_8$-cycloalkyl, $C_5$–$C_{10}$-bicycloalkyl, phenyl, naphthyl, or 5- or 6-membered heterocyclyl, containing one to four nitrogen atoms or one to three nitrogen atoms and one sulfur or oxygen atom, or
  5- or 6-membered heteroaryl, containing one to four nitrogen atoms or one to three nitrogen atoms and one sulfur or oxygen atom, or
  where $R^1$ and $R^2$ radicals may be unsubstituted or partially or fully halogenated or may carry one to three groups $R^a$,
  $R^a$ is halogen, cyano, nitro, hydroxyl, $C_1$–$C_6$-alkyl, $C_1$–$C_6$-haloalkyl, $C_3$–$C_6$-cycloalkyl, $C_1$–$C_6$-alkoxy, $C_1$–$C_6$-haloalkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkynyl, $C_3$–$C_6$-alkynyloxy and $C_1$–$C_4$-alkylenedioxy, which may be halogenated; or
  $R^1$ and $R^2$ together with the interjacent nitrogen atom represent a 5- or 6-membered heterocyclic ring, containing one to four nitrogen atoms or one to three nitrogen atoms and one sulfur or oxygen atom, which may be substituted by one to three $R^a$ radicals;
- X is cyano, $C_1$–$C_6$-alkoxy, $C_1$–$C_6$-haloalkoxy or $C_3$–$C_8$-alkenyloxy.

Moreover, the invention relates to processes for their preparation, compositions containing them and to their use for combating phytopathogenic fungi.

EP-A 071 792 discloses 6-phenyl-7-amino-triazolopyrimidines where the 5-position is substituted by hydrogen or alkyl or aryl groups.

EP-A 550 113 relates to 5-H- and 5-halogen-6-phenyl-7-amino-tri-azolopyrimidines where the 7-amino group is further substituted.

WO-A 98/46607 discloses triazolopyrimidines, which are substituted in the 6-position by a 2,4,6-trifluorophenyl group.

U.S. Pat. No. 5,994,360 discloses triazolopyrimidines, which are substituted in the 5-position by alkyl groups.

The compounds disclosed in the documents discussed above are said to be active against various phytopathogenic fungi.

It is an object of the present invention to provide compounds having improved fungicidal activity.

We have found that this object is achieved by the compounds defined at the outset. Furthermore, we have found processes for their preparation, compositions comprising them and methods for controlling phytopathogenic fungi using the compounds I.

The compounds of the formula I differ from the compounds known from the abovementioned art in the combination of the 2-chloro-6-fluoro-phenyl group and a specific substitution in 5-position of the triazolopyrimidine system.

A 4- to 6-membered heterocyclic group may be any heterocyclic group with 4 to 6 ring atoms, interrupted by one or more heteroatoms selected from sulfur, nitrogen, and oxygen, preferably oxygen. A halogen atom suitable denotes a fluorine, chlorine or bromine atom.

The present invention further provides a process for the preparation of compounds of formula I as defined above which comprises treating a 5-halogen compound of formula II

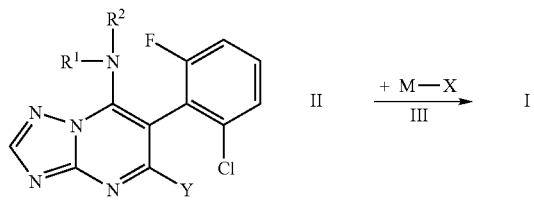

in which Y is halogen with a compound of formula III, which is, dependent from the value of X to be introduced to yield formula I compounds, an anorganic cyano salt, an alkoxylate, haloalkoxylate or an alkenyloxylate, respectively, preferably in the presence of a a solvent. The cation M in formula III has minor influence; for practical and economical reasons usually ammonium-, tetraalkylammonium- or alkalimetal- and earth metal salts are preferred.

Suitable solvents include ethers, such as dioxane, diethyl ether and, especially, tetrahydrofuran, halogenated hydrocarbons such as dichloromethane and aromatic hydrocarbons, for example toluene.

The reaction is suitably carried out at a temperature in the range from 0 to 120° C., the preferred reaction temperature being from 10 to 40° C.

It is also preferred that the reaction is carried out in the presence of a base. Suitable bases include tertiary amines, such as triethylamine, and inorganic bases, such as potassium carbonate or sodium carbonate. Alternatively, an excess of the compound of formula III may serve as a base.

The reaction mixtures are worked up in a customary manner, for example by mixing with water, phase separation and, if required, chromatographic purification of the crude products. Some of the end products are obtained in the form of colorless or slightly brownish, viscous oils, which are purified or freed from volatile components under reduced pressure and at moderately elevated temperatures. If the end products are obtained as solids, purification can also be carried out by recrystallization or digestion.

Compounds of formula II are known in the art and can be obtained by synthesis routes disclosed in EP-A 550 113 and WO-A 98/46608.

If individual compounds I are not obtainable by the routes described above, they can be prepared by derivatization of other compounds I.

In the symbol definitions given in the formulae above, collective terms were used which generally represent the following substituents:

halogen: fluorine, chlorine, bromine and iodine;

$C_1$–$C_{10}$-alkyl and the alkyl moieties of $C_1$–$C_{10}$-haloalkyl: saturated, straight-chain or branched hydrocarbon radicals having 1 to 10, especially 1 to 6 carbon atoms, for example $C_1$–$C_4$-alkyl as mentioned above or pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$–$C_6$-haloalkyl and the haloalkyl moieties of $C_1$–$C_6$-haloalkoxy: straight-chain or branched alkyl groups having 1 to 6, preferably 1 to 4 carbon atoms (as mentioned above), where the hydrogen atoms in these groups may be partially or fully replaced by halogen atoms as mentioned above, for example $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_3$–$C_{10}$-alkenyl: unsaturated, straight-chain or branched hydrocarbon radicals having 3 to 10, especially 3 to 6 carbon atoms and a double bond in any position, for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl;

$C_2$–$C_{10}$-alkynyl: straight-chain or branched hydrocarbon radicals having 2 to 10, especially 2 to 4 carbon atoms and a triple bond in any position, for example ethynyl, 1-propynyl, 2-propynyl, 1-butynyl, 2-butynyl, 3-butynyl and 1-methyl-2-propynyl;

In general terms, the term cycloalkyl, as used herein with respect to a radical or moiety refers to a cycloalkyl group having 3 to 8 carbon atoms, preferably 5 to 7 carbon atoms.

In general terms, the term bicycloalkyl, as used herein with respect to a radical or moiety refers to a bicycloalkyl group having 5 to 10 carbon atoms, preferably 6 to 9 carbon atoms, in particular bicycloheptyl being optionally substituted by one or more halogen atoms, nitro, cyano, alkyl, preferably $C_{1-6}$ alkyl, alkoxy, preferably $C_{1-6}$ alkoxy.

5-membered heteroaryl, containing one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl, containing one to four nitrogen atoms: 6-membered heteroaryl groups which, in addition to carbon atoms, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

With respect to their intended use, preference is given to triazolopyrimidines of the formula I having the following substituents, where the preference is valid in each case on its own or in combination:

The particularly preferred embodiments of the intermediates with respect to the variables correspond to those of the radicals X, $R^1$ and $R^2$ of formula I.

A preferred alkyl moiety is an ethyl or especially a methyl group.

A preferred haloalkyl moiety is the 2,2,2-trifluoroethyl or 1,1,1-trifluoroprop-2-yl group;

A preferred alkenyl moiety is allyl or especially a 2-methylallyl group.

A preferred cycloalkyl moiety is cyclopentyl being optionally substituted by one or more halogen atoms, nitro, cyano, alkyl, preferably $C_1$–$C_6$ alkyl, alkoxy, preferably $C_1$–$C_6$ alkoxy.

A preferred heteroaryl moiety is pyridyl, pyrimidyl, pyrazolyl or thienyl.

Preference is given to compounds of formula I in which any alkyl or haloalkyl part of the groups $R^1$ or $R^2$, which may be straight chained or branched, contains up to 10 carbon atoms, preferably 1 to 9 carbon atoms, more preferably 2 to 6 carbon atoms, any alkenyl or alkynyl part of the substituents $R^1$ or $R^2$ contains up to 10 carbon atoms, preferably 2 to 9 carbon atoms, more preferably 3 to 6 carbon atoms, any cycloalkyl part of the substituents $R^1$ or $R^2$ contains from 3 to 10 carbon atoms, preferably from 3 to 8 carbon atoms, more preferably from 3 to 6 carbon atoms, and any: bicycloalkyl part of the substituents $R^1$ or $R^2$ contains from 5 to 9 carbon atoms, preferably from 7 to 9 carbon atoms. Any alkyl, alkenyl or alkynyl group may be linear or branched.

Likewise, preference is given to compounds of formula I wherein $R^1$ is not hydrogen.

Compounds of formula I are preferred in which $R^1$ represents a straight-chained or branched $C_1$–$C_{10}$-alkyl, in particular a branched $C_3$–$C_{10}$-alkyl group, a $C_3$–$C_8$-cycloalkyl, a $C_5$–$C_9$-bicycloalkyl, a $C_3$–$C_8$-cycloalkyl-$C_1$–$C_6$-alkyl, $C_1$–$C_{10}$-alkoxy-$C_1$–$C_6$-alkyl, a $C_1$–$C_{10}$-haloalkyl or a phenyl group being optionally substituted by one to three halogen atoms or $C_1$–$C_{10}$-alkyl or $C_1$–$C_{10}$-alkoxy groups.

Particular preference is given to compounds I in which $R^2$ represents a hydrogen atom, a $C_1$–$C_{10}$-alkyl or a $C_1$–$C_{10}$-haloalkyl group, in particular a hydrogen atom.

Besides, particular preference is given to compounds I in which $R^2$ is hydrogen.

Moreover, particular preference is given to compounds I in which $R^2$ is methyl.

Furthermore, particular preference is given to compounds I in which $R^2$ is ethyl.

If $R^1$ denotes a $C_1$–$C_{10}$-haloalkyl group, preferably a polyfluorinated alkyl group, in particular a 2,2,2-trifluoroethyl, a 2-(1,1,1-trifluoropropyl) or a 2-(1,1,1-trifluorobutyl) group, $R^2$ preferably represents a hydrogen atom.

If $R^1$ denotes an optionally substituted $C_3$–$C_8$-cycloalkyl group, preferably a cyclopentyl or cyclohexyl group, $R^2$ preferably represents a hydrogen atom or $C_1$–$C_6$-alkyl group.

Moreover, particular preference is given to compounds I in which $R^1$ and $R^2$ together with the interjacent nitrogen atom form an optionally substituted heterocyclic ring, preferably an optionally substituted $C_3$–$C_7$-heterocyclic ring, in particular a pyrrolidine, piperidine, tetrahydropyridine, in particular 1,2,3,6-tetrahydropyridine or azepane ring which is optionally substituted by one or more $C^1$–$C_{10}$-alkyl groups.

Included in the scope of the present invention are (R) and (S) isomers of compounds of general formula I having a chiral center and the racemates thereof, and salts, N-oxides and acid addition compounds.

With respect to their use, particular preference is given to the compounds I compiled in the tables below. The groups mentioned in the tables for a substituent are furthermore for their part, independently of the combination in which they are mentioned, a particularly preferred embodiment of the respective substituents.

Table 1
Compounds of the formula I, in which X is cyano and $R^1$ and $R^2$ correspond to one row in Table A Table 2
Compounds of the formula I, in which X is methoxy and $R^1$ and $R^2$ correspond to one row in Table A Table 3
Compounds of the formula I, in which X is ethoxy and $R^1$ and $R^2$ correspond to one row in Table A Table 4
Compounds of the formula I, in which X is n-propoxy and $R^1$ and $R^2$ correspond to one row in Table A Table 5
Compounds of the formula I, in which X is iso-propoxy and $R^1$ and $R^2$ correspond to one row in Table A Table 6
Compounds of the formula 1, in which X is allyloxy and $R^1$ and $R^2$ correspond to one row in Table A Table 7
Compounds of the formula I, in which X is 3-methylallyloxy and $R^1$ and $R^2$ correspond to one row in Table A Table 8
Compounds of the formula I, in which X is fluoromethoxy and $R^1$ and $R^2$ correspond to one row in Table A Table 9
Compounds of the formula I, in which X is difluoromethoxy and $R^1$ and $R^2$ correspond to one row in Table A Table 10
Compounds of the formula I, in which X is trifluoromethoxy and $R^1$ and $R^2$ correspond to one row in Table A

TABLE A

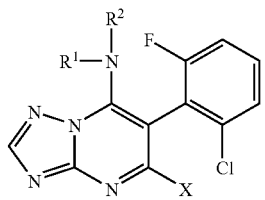

I

| No. | $R^1$ | $R^2$ |
|---|---|---|
| A-1 | $CH_2CH_3$ | H |
| A-2 | $CH_2CH_3$ | $CH_3$ |
| A-3 | $CH_2CH_3$ | $CH_2CH_3$ |
| A-4 | $CH_2CF_3$ | H |
| A-5 | $CH_2CF_3$ | $CH_3$ |
| A-6 | $CH_2CF_3$ | $CH_2CH_3$ |
| A-7 | $CH_2CCl_3$ | H |
| A-8 | $CH_2CCl_3$ | $CH_3$ |
| A-9 | $CH_2CCl_3$ | $CH_2CH_3$ |
| A-10 | $CH_2CH_2CH_3$ | H |
| A-11 | $CH_2CH_2CH_3$ | $CH_3$ |
| A-12 | $CH_2CH_2CH_3$ | $CH_2CH_3$ |
| A-13 | $CH_2CH_2CH_3$ | $CH_2CH_2CH_3$ |
| A-14 | $CH(CH_3)_2$ | H |
| A-15 | $CH(CH_3)_2$ | $CH_3$ |
| A-16 | $CH(CH_3)_2$ | $CH_2CH_3$ |
| A-17 | (±) $CH(CH_3)$—$CH_2CH_3$ | H |
| A-18 | (±) $CH(CH_3)$—$CH_2CH_3$ | $CH_3$ |
| A-19 | (±) $CH(CH_3)$—$CH_2CH_3$ | $CH_2CH_3$ |
| A-20 | (R) $CH(CH_3)$—$CH_2CH_3$ | H |
| A-21 | (R) $CH(CH_3)$—$CH_2CH_3$ | $CH_3$ |
| A-22 | (R) $CH(CH_3)$—$CH_2CH_3$ | $CH_2CH_3$ |
| A-23 | (S) $CH(CH_3)$—$CH_2CH_3$ | H |
| A-24 | (S) $CH(CH_3)$—$CH_2CH_3$ | $CH_3$ |
| A-25 | (S) $CH(CH_3)$—$CH_2CH_3$ | $CH_2CH_3$ |
| A-26 | (±) $CH(CH_3)$—$CH(CH_3)_2$ | H |
| A-27 | (±) $CH(CH_3)$—$CH(CH_3)_2$ | $CH_3$ |
| A-28 | (±) $CH(CH_3)$—$CH(CH_3)_2$ | $CH_2CH_3$ |
| A-29 | (R) $CH(CH_3)$—$CH(CH_3)_2$ | H |
| A-30 | (R) $CH(CH_3)$—$CH(CH_3)_2$ | $CH_3$ |
| A-31 | (R) $CH(CH_3)$—$CH(CH_3)_2$ | $CH_2CH_3$ |
| A-32 | (S) $CH(CH_3)$—$CH(CH_3)_2$ | H |
| A-33 | (S) $CH(CH_3)$—$CH(CH_3)_2$ | $CH_3$ |
| A-34 | (S) $CH(CH_3)$—$CH(CH_3)_2$ | $CH_2CH_3$ |
| A-35 | (±) $CH(CH_3)$—$C(CH_3)_3$ | H |
| A-36 | (±) $CH(CH_3)$—$C(CH_3)_3$ | $CH_3$ |
| A-37 | (±) $CH(CH_3)$—$C(CH_3)_3$ | $CH_2CH_3$ |
| A-38 | (R) $CH(CH_3)$—$C(CH_3)_3$ | H |
| A-39 | (R) $CH(CH_3)$—$C(CH_3)_3$ | $CH_3$ |
| A-40 | (R) $CH(CH_3)$—$C(CH_3)_3$ | $CH_2CH_3$ |
| A-41 | (S) $CH(CH_3)$—$C(CH_3)_3$ | H |
| A-42 | (S) $CH(CH_3)$—$C(CH_3)_3$ | $CH_3$ |
| A-43 | (S) $CH(CH_3)$—$C(CH_3)_3$ | $CH_2CH_3$ |
| A-44 | (±) $CH(CH_3)$—$CF_3$ | H |
| A-45 | (±) $CH(CH_3)$—$CF_3$ | $CH_3$ |
| A-46 | (±) $CH(CH_3)$—$CF_3$ | $CH_2CH_3$ |
| A-47 | (R) $CH(CH_3)$—$CF_3$ | H |
| A-48 | (R) $CH(CH_3)$—$CF_3$ | $CH_3$ |
| A-49 | (R) $CH(CH_3)$—$CF_3$ | $CH_2CH_3$ |
| A-50 | (S) $CH(CH_3)$—$CF_3$ | H |
| A-51 | (S) $CH(CH_3)$—$CF_3$ | $CH_3$ |
| A-52 | (S) $CH(CH_3)$—$CF_3$ | $CH_2CH_3$ |
| A-53 | (±) $CH(CH_3)$—$CCl_3$ | H |
| A-54 | (±) $CH(CH_3)$—$CCl_3$ | $CH_3$ |
| A-55 | (±) $CH(CH_3)$—$CCl_3$ | $CH_2CH_3$ |
| A-56 | (R) $CH(CH_3)$—$CCl_3$ | H |
| A-57 | (R) $CH(CH_3)$—$CCl_3$ | $CH_3$ |
| A-58 | (R) $CH(CH_3)$—$CCl_3$ | $CH_2CH_3$ |
| A-59 | (S) $CH(CH_3)$—$CCl_3$ | H |
| A-60 | (S) $CH(CH_3)$—$CCl_3$ | $CH_3$ |
| A-61 | (S) $CH(CH_3)$—$CCl_3$ | $CH_2CH_3$ |
| A-62 | $CH_2C(CH_3)$=$CH_2$ | H |
| A-63 | $CH_2C(CH_3)$=$CH_2$ | $CH_3$ |
| A-64 | $CH_2C(CH_3)$=$CH_2$ | $CH_2CH_3$ |
| A-65 | cyclopentyl | H |
| A-66 | cyclopentyl | $CH_3$ |
| A-67 | cyclopentyl | $CH_2CH_3$ |
| A-68 | —$(CH_2)_2CH(CH_3)(CH_2)_2$— | |

The compounds I are suitable as fungicides. They have outstanding activity against a broad spectrum of phytopathogenic fungi, in particular from the classes of the *Ascomycetes, Deuteromycetes, Phycomycetes* and *Basidiomiycetes*. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

*Alternaria* species on vegetables and fruit,
*Botrytis cinerea* (gray mold) on strawberries, vegetables, ornamentals and grapevines,
*Cercospora arachidicola* on peanuts,
*Erysiphe cichoracearum* and *Sphaerotheca fuliginea* on cucurbits,
*Blumeria graminis* (powdery mildew) on cereals,
*Fusarium* and *Verticillium* species on various plants,
*Helminthosporium* species on cereals,
*Mycosphaerella* species on bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawns,
*Septoria* species in cereals,
*Uncinula necator* on grapevines,
*Ustilago* species on cereals and sugar cane, and
*Venturia* species (scab) on apples and pears.

Moreover, the compounds I are suitable for controlling harmful fungi such as *Paecilomyces variotii* in the protection of materials (e.g. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

The compounds I can be converted into the customary formulations, e.g. solutions, emulsions, suspensions, dusts, powders, pastes and granules. The use form depends on the particular purpose; in any case, it should guarantee a fine and uniform distribution of the compound according to the invention.

The formulations are prepared in a known manner, e.g. by extending the active ingredient with solvents and/or carriers, if desired using emulsifiers and dispersants, it also being possible to use other organic solventsas auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such asground natural minerals (e.g. kaolins, clays, talc, chalk) and ground synthetic minerals (e.g. highly-disperse silica, silicates); emulsifiers such as non-ionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, impregnated granules and homogeneous granules, can be prepared by binding the active ingredients to solid carriers. Examples of solid carriers are mineral earths, such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-a-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides., fungicides, other pesticides, or bactericides may be added to the active ingredients, if appropriate also only immediately prior to use (tank mix). These agents can be admixed with the agents according to the invention in a weight ratio of 1:10 to 10:1.

In the use form as fungicides, the compositions according to the invention can also be present together with other active ingredients, e.g. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides, together with which the compounds according to the invention can be used, is intended to illustrate the possible combinations, but not to impose any limitation:

sulfur, dithiocarbamates and their derivatives, such as iron (III) dime thyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'- propylenebisdithiocarbamate), zinc (N,N'-propylenebisdithiocarbamate), N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfo-diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane; 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]-piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurines such as azoxystrobin, kresoxim methyl, methyl-E-methoxyimino-[α-(2-phenoxyphenyl)]-acetamide, methyl E-methoxyimino-[α-(2,5-dimethylphenoxyl)-o-tolyl]acetamide, picoxystrobin, pyraclostrobin, trifloxystrobin, anilinopyrimidines such as N-(4,6-dimethylpyrimidin-2-yl)aniline, N-[4-methyl-6-(1-propynyl)pyrimidin-2-yl]-aniline, N-[4-methyl-6-cyclopropylpyrimidin-2-yl]aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxyphenyl)acryloylmorpholine, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-amino-butyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichloro-phenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

SYNTHESIS EXAMPLES

With due modification of the starting compounds, the protocol shown in the synthesis example below was used for obtaining further compounds I. The resulting compounds I, together with physical data, are listed in the Table I which follows. Further 5-chloro compounds of formula II which were used for obtaining said further compounds I are listed in following Table II.

Example 1

Preparation of 5-cyano-6-(2-chloro-6-fluorophenyl)-7-isopropylamino-[1,2,4]-triazolo[1,5-α]pyrimidine A mixture of 0.1 mol 5-chloro-6-(2-chloro-6-fluorophenyl)-7-isopropylamino-[1,2,4]-triazolo[1,5-α]pyrimidine [cf. EP-A 550 113] and 0.25 mol tetraethylammonium cyanide in 750 ml dimethylformamde was stirred for about 16 hours at 20 to 25° C. To this mixture water and methyl-tert. butyl ether were added, the organic phase was separated, washed with water, dried and filtered. Distillative removal of the solvent from the filtrate and chromatography over silica gel gave 7.1 g of the title compound of mp. 159° C.

Example 2

Preparation of 5-methoxy-6-(2-chloro-6-fluorophenyl)-7-isopropylamino-[1,2,4]-triazolo[1,5-α]pyrimidine To a solution of 65 mmol 5-chloro-6-(2-chloro-6-fluorophenyl)-7-(4-methylpiperidin-1-yl)-[1,2,4]-triazolo[1,5-α]pyrimidine [cf. EP-A 550 113] in dry methanol 71.5 mmol of a 30% solution of sodium methanolate were added at 20 to 25° C. After having stirred this mixture for about 16 hours at this temperature methanol ws evaporated nad the residue was dissolved with dichloromethane. The organic phase was separated, washed with water, dried and filtered. Distillative removal of the solvent from the filtrate and chromatography over silica gel gave 4.2 g of the title compound of mp. 182° C.

TABLE I

I

| No. | R¹ | R² | X | phys. data (m.p. [° C.], IR [cm⁻¹]) |
|---|---|---|---|---|
| I-1 | CH₂C(CH₃)=CH₂ | CH₂CH₃ | CN | 139 |
| I-2 | CH(CH₃)₂ | H | CN | 159 |
| I-3 | —(CH₂)₂CH(CH₃)(CH₂)₂— | | CN | 196 |
| I-4 | cyclopentyl | H | CN | |
| I-5 | CH₂CH₃ | CH₂CH₃ | CN | 212 |
| I-6 | CH₂CH₂CH₃ | CH₂CH₂CH₃ | CN | |
| I-7 | CH(CH₃)₂ | CH₃ | CN | |
| I-8 | (±) CH(CH₃)—CH₂CH₃ | H | CN | |
| I-9 | (S) CH(CH₃)—CH₂CH₃ | H | CN | |
| I-10 | (R) CH(CH₃)—CH₂CH₃ | H | CN | |
| I-11 | (±) CH(CH₃)—CH(CH₃)₂ | H | CN | |
| I-12 | (S) CH(CH₃)—CH(CH₃)₂ | H | CN | |
| I-13 | (R) CH(CH₃)—CH(CH₃)₂ | H | CN | |
| I-14 | (±) CH(CH₃)—CH(CH₃)₃ | H | CN | |
| I-15 | (S) CH(CH₃)—CH(CH₃)₃ | H | CN | |
| I-16 | (R) CH(CH₃)—CH(CH₃)₃ | H | CN | |
| I-17 | (±) CH(CH₃)—CF₃ | H | CN | |
| I-18 | (S) CH(CH₃)—CF₃ | H | CN | |
| I-19 | (R) CH(CH₃)—CF₃ | H | CN | |
| I-20 | CH₂CF₃ | H | CN | |
| I-21 | CH₂C(CH₃)=CH₂ | CH₂CH₃ | OCH₃ | |
| I-22 | CH(CH₃)₂ | H | OCH₃ | |
| I-23 | —(CH₂)₂CH(CH₃)(CH₂)₂— | | OCH₃ | 182 |
| I-24 | cyclopentyl | H | OCH₃ | |
| I-25 | CH₂CH₃ | CH₂CH₃ | OCH₃ | |
| I-26 | CH₂CH₂CH₃ | CH₂CH₂CH₃ | OCH₃ | |
| I-27 | CH(CH₃)₂ | CH₃ | OCH₃ | |
| I-28 | (±) CH(CH₃)—CH₂CH₃ | H | OCH₃ | |
| I-29 | (S) CH(CH₃)—CH₂CH₃ | H | OCH₃ | |
| I-30 | (R) CH(CH₃)—CH₂CH₃ | H | OCH₃ | |
| I-31 | (±) CH(CH₃)—CH(CH₃)₂ | H | OCH₃ | |
| I-32 | (S) CH(CH₃)—CH(CH₃)₂ | H | OCH₃ | |
| I-33 | (R) CH(CH₃)—CH(CH₃)₂ | H | OCH₃ | |
| I-34 | (±) CH(CH₃)—CH(CH₃)₃ | H | OCH₃ | |
| I-35 | (S) CH(CH₃)—CH(CH₃)₃ | H | OCH₃ | |
| I-36 | (R) CH(CH₃)—CH(CH₃)₃ | H | OCH₃ | |
| I-37 | (±) CH(CH₃)—CF₃ | H | OCH₃ | |
| I-38 | (S) CH(CH₃)—CF₃ | H | OCH₃ | |
| I-39 | (R) CH(CH₃)—CF₃ | H | OCH₃ | |
| I-40 | CH₂CF₃ | H | OCH₃ | |
| I-41 | CH₂C(CH₃)=CH₂ | CH₂CH₃ | OCH₂CH₃ | |
| I-42 | CH(CH₃)₂ | H | OCH₂CH₃ | |
| I-43 | —(CH₂)₂CH(CH₃)(CH₂)₂— | | OCH₂CH₃ | 135 |
| I-44 | cyclopentyl | H | OCH₂CH₃ | |
| I-45 | CH₂CH₃ | CH₂CH₃ | OCH₂CH₃ | |
| I-46 | CH₂CH₂CH₃ | CH₂CH₂CH₃ | OCH₂CH₃ | |
| I-47 | CH(CH₃)₂ | CH₃ | OCH₂CH₃ | |
| I-48 | (±) CH(CH₃)—CH₂CH₃ | H | OCH₂CH₃ | |
| I-49 | (S) CH(CH₃)—CH₂CH₃ | H | OCH₂CH₃ | |
| I-50 | (R) CH(CH₃)—CH₂CH₃ | H | OCH₂CH₃ | |
| I-51 | (±) CH(CH₃)—CH(CH₃)₂ | H | OCH₂CH₃ | |
| I-52 | (S) CH(CH₃)—CH(CH₃)₂ | H | OCH₂CH₃ | |
| I-53 | (R) CH(CH₃)—CH(CH₃)₂ | H | OCH₂CH₃ | |
| I-54 | (±) CH(CH₃)—CH(CH₃)₃ | H | OCH₂CH₃ | |
| I-55 | (S) CH(CH₃)—CH(CH₃)₃ | H | OCH₂CH₃ | |
| I-56 | (R) CH(CH₃)—CH(CH₃)₃ | H | OCH₂CH₃ | |
| I-57 | (±) CH(CH₃)—CF₃ | H | OCH₂CH₃ | |
| I-58 | (S) CH(CH₃)—CF₃ | H | OCH₂CH₃ | |
| I-59 | (R) CH(CH₃)—CF₃ | H | OCH₂CH₃ | |
| I-60 | CH₂CF₃ | H | OCH₂CH₃ | |
| I-61 | CH₂C(CH₃)=CH₂ | CH₂CH₃ | OCH(CH₃)₂ | |

TABLE I-continued

I

| No. | R¹ | R² | X | phys. data (m.p. [° C.], IR [cm⁻¹]) |
|---|---|---|---|---|
| I-62 | CH(CH₃)₂ | H | OCH(CH₃)₂ | |
| I-63 | —(CH₂)₂CH(CH₃)(CH₂)₂— | | OCH(CH₃)₂ | 156 |
| I-64 | cyclopentyl | H | OCH(CH₃)₂ | |
| I-65 | CH₂CH₃ | CH₂CH₃ | OCH(CH₃)₂ | 102 |
| I-66 | CH₂CH₂CH₃ | CH₂CH₂CH₃ | OCH(CH₃)₂ | |
| I-67 | CH(CH₃)₂ | CH₃ | OCH(CH₃)₂ | |
| I-68 | (±) CH(CH₃)—CH₂CH₃ | H | OCH(CH₃)₂ | |
| I-69 | (S) CH(CH₃)—CH₂CH₃ | H | OCH(CH₃)₂ | |
| I-70 | (R) CH(CH₃)—CH₂CH₃ | H | OCH(CH₃)₂ | |
| I-71 | (±) CH(CH₃)—CH(CH₃)₂ | H | OCH(CH₃)₂ | |
| I-72 | (S) CH(CH₃)—CH(CH₃)₂ | H | OCH(CH₃)₂ | |
| I-73 | (R) CH(CH₃)—CH(CH₃)₂ | H | OCH(CH₃)₂ | |
| I-74 | (±) CH(CH₃)—CH(CH₃)₃ | H | OCH(CH₃)₂ | |
| I-75 | (S) CH(CH₃)—CH(CH₃)₃ | H | OCH(CH₃)₂ | |
| I-76 | (R) CH(CH₃)—CH(CH₃)₃ | H | OCH(CH₃)₂ | |
| I-77 | (±) CH(CH₃)—CF₃ | H | OCH(CH₃)₂ | |
| I-78 | (S) CH(CH₃)—CF₃ | H | OCH(CH₃)₂ | |
| I-79 | (R) CH(CH₃)—CF₃ | H | OCH(CH₃)₂ | |
| I-80 | CH₂CF₃ | H | OCH(CH₃)₂ | |
| I-81 | CH₂C(CH₃)=CH₂ | CH₂CH₃ | OCH₂CH=CH₂ | |
| I-82 | CH(CH₃)₂ | H | OCH₂CH=CH₂ | |
| I-83 | —(CH₂)₂CH(CH₃)(CH₂)₂— | | OCH₂CH=CH₂ | 2990, 1655, 985 |
| I-84 | cyclopentyl | H | OCH₂CH=CH₂ | |
| I-85 | CH₂CH₃ | CH₂CH₃ | OCH₂CH=CH₂ | |
| I-86 | CH₂CH₂CH₃ | CH₂CH₂CH₃ | OCH₂CH=CH₂ | |
| I-87 | CH(CH₃)₂ | CH₃ | OCH₂CH=CH₂ | |
| I-88 | (±) CH(CH₃)—CH₂CH₃ | H | OCH₂CH=CH₂ | |
| I-89 | (S) CH(CH₃)—CH₂CH₃ | H | OCH₂CH=CH₂ | |
| I-90 | (R) CH(CH₃)—CH₂CH₃ | H | OCH₂CH=CH₂ | |
| I-91 | (±) CH(CH₃)—CH(CH₃)₂ | H | OCH₂CH=CH₂ | |
| I-92 | (S) CH(CH₃)—CH(CH₃)₂ | H | OCH₂CH=CH₂ | |
| I-93 | (R) CH(CH₃)—CH(CH₃)₂ | H | OCH₂CH=CH₂ | |
| I-94 | (±) CH(CH₃)—CH(CH₃)₃ | H | OCH₂CH=CH₂ | |
| I-95 | (S) CH(CH₃)—CH(CH₃)₃ | H | OCH₂CH=CH₂ | |
| I-96 | (R) CH(CH₃)—CH(CH₃)₃ | H | OCH₂CH=CH₂ | |
| I-97 | (±) CH(CH₃)—CF₃ | H | OCH₂CH=CH₂ | |
| I-98 | (S) CH(CH₃)—CF₃ | H | OCH₂CH=CH₂ | |
| I-99 | (R) CH(CH₃)—CF₃ | H | OCH₂CH=CH₂ | |
| I-100 | CH₂CF₃ | H | OCH₂CH=CH₂ | |
| I-101 | CH₂C(CH₃)=CH₂ | CH₂CH₃ | OCHF₂ | |
| I-102 | CH(CH₃)₂ | H | OCHF₂ | |
| I-103 | —(CH₂)₂CH(CH₃)(CH₂)₂— | | OCHF₂ | 138 |
| I-104 | cyclopentyl | H | OCHF₂ | |
| I-105 | CH₂CH₃ | CH₂CH₃ | OCHF₂ | |
| I-106 | CH₂CH₂CH₃ | CH₂CH₂CH₃ | OCHF₂ | |
| I-107 | CH(CH₃)₂ | CH₃ | OCHF₂ | |
| I-108 | (±) CH(CH₃)—CH₂CH₃ | H | OCHF₂ | |
| I-109 | (S) CH(CH₃)—CH₂CH₃ | H | OCHF₂ | |
| I-110 | (R) CH(CH₃)—CH₂CH₃ | H | OCHF₂ | |
| I-111 | (±) CH(CH₃)—CH(CH₃)₂ | H | OCHF₂ | |
| I-112 | (S) CH(CH₃)—CH(CH₃)₂ | H | OCHF₂ | |
| I-113 | (R) CH(CH₃)—CH(CH₃)₂ | H | OCHF₂ | |
| I-114 | (±) CH(CH₃)—CH(CH₃)₃ | H | OCHF₂ | |
| I-115 | (S) CH(CH₃)—CH(CH₃)₃ | H | OCHF₂ | |
| I-116 | (R) CH(CH₃)—CH(CH₃)₃ | H | OCHF₂ | |
| I-117 | (±) CH(CH₃)—CF₃ | H | OCHF₂ | |
| I-118 | (S) CH(CH₃)—CF₃ | H | OCHF₂ | |
| I-119 | (R) CH(CH₃)—CF₃ | H | OCHF₂ | |
| I-120 | CH₂CF₃ | H | OCHF₂ | |

TABLE II

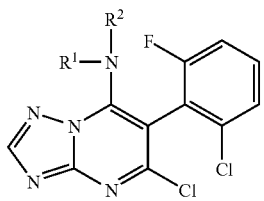

| No. | R¹ | R² | phys. data (m.p. [° C.]) |
|---|---|---|---|
| II-1 | CH₂C(CH₃)=CH₂ | CH₂CH₃ | 136 |
| II-2 | CH(CH₃)₂ | H | 143 |
| II-3 | —(CH₂)₂CH(CH₃) (CH₂)₂— | | 150 |
| II-4 | cyclopentyl | H | 62 |
| II-5 | CH₂CH₃ | CH₂CH₃ | 167 |
| II-6 | CH₂CH₂CH₃ | CH₂CH₂CH₃ | 148 |
| II-7 | CH(CH₃)₂ | CH₃ | 151 |
| II-8 | (±) CH(CH₃)—CH₂CH₃ | H | 150 |
| II-9 | (S) CH(CH₃)—CH₂CH₃ | H | 147 |
| II-10 | (R) CH(CH₃)—CH₂CH₃ | H | 147 |
| II-11 | (±) CH(CH₃)—CH(CH₃)₂ | H | 145 |
| II-12 | (S) CH(CH₃)—CH(CH₃)₂ | H | 145 |
| II-13 | (R) CH(CH₃)—CH(CH₃)₂ | H | 145 |
| II-14 | (±) CH(CH₃)—CH(CH₃)₂ | H | 188 |
| II-15 | (S) CH(CH₃)—CH(CH₃)₃ | H | 191 |
| II-16 | (R) CH(CH₃)—CH(CH₃)₃ | H | 191 |
| II-17 | (±) CH(CH₃)—CF₃ | H | 179 |
| II-18 | (S) CH(CH₃)—CF₃ | H | 172 |
| II-19 | (R) CH(CH₃)—CF₃ | H | 172 |
| II-20 | CH₂CF₃ | H | 211 |
| II-21 | H | H | 250 |

Examples of the action against harmful fungi

The fungicidal action of the compounds of the formula I was demonstrated by the following experiments:

The active compounds, separately or together, were formulated as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to the desired concentration.

Use Example 1: Action on *Alternaria solani* in Tomatoes

Leaves of pot grown tomato seedlings of the "Große Fleischtomate St. Pierre" variety were sprayed with aqueous liquors made from a stock solution consisting of 10% of active ingredient, 63% of cyclohexanone, and 27% of emulsifier. After 24 hours the leaves were infected with a zoospore suspension of *Alternaria solani* (1.7×10⁶ spores per ml of a 2% strength biomalt solution). The plants were then placed in a water vapour-saturated chamber. After 5 days the disease had spread to such a great extent on the untreated plants that the fungicidal activity of the substances could be assessed.

In this test, the plants which had been treated with 63 ppm of compounds I-1, I-3, and I-23 showed an infection of up to 3%, whereas the untreated plants were infected to 100%.

Use Example 2: Action on *Plasmopara viticola*

Leaves of potted vines of the "Müller Thurgau" variety were sprayed with aqueous liquors made from a stock solution consisting of 10% of active ingredient, 63% of cyclohexanone, and 27% of emulsifier. To assess the duration of action, the plants were set up, after the sprayed-on layer had dried, in the greenhouse for 8 days. Then the leaves were infected with a zoospore suspension of the fungus *Plasmopara viticola*, first placed in a vapour-saturated chamber at 24° C., and then kept for 5 days in a greenhouse at 20 to 30° C. To accelerate and intensify the sporangiophore discharge, the plants were then again placed in the moist chamber for 16 hours. The extent of fungus attack was then assessed on the undersides of the leaves.

In this test, the plants which had been treated with 250 ppm of compounds I-1 and I-2 showed an infection of up to 20%, whereas the untreated plants were infected to 85%.

Active compounds A to E known from EP-A 550 113, WO-A 99/41255, and U.S. Pat. No. 5,994,360 resp., were used as comparison compounds in the following comparison tests:

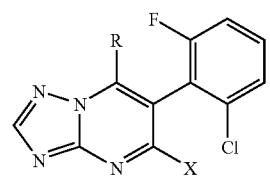

| No. | known from | R | X |
|---|---|---|---|
| A | EP-A 550 113, No. 106 | isopropylamino | chloro |
| B | EP-A 550 113, No. 111 | diethylamino | chloro |
| C | WO-A 99/41255, No. 38 | cyclohexyl | methoxy |
| D | WO-A 99/41255, No. 39 | cyclohexyl | cyano |
| E | U.S. Pat. No. 5,994,360, Ex. 1B | 4-CH₃-piperidine | methyl |

Comparison Test 1: Fungicidal Control of Early Blight on Tomatoes (*Alternaria solani*)

Young seedlings of tomato plants of the variety "Große Fleischtomate St. Pierre" were grown in pots to the 2 to 4 leaf stage. These plants were sprayed to run-off with an aqueous suspension, containing the concentration of active ingredient mentioned in the table below, prepared from a stock solution containing 10% of the active ingredient, 85% cyclohexanone and 5% emulsifier. The next day, the treated plants were inoculated with an aqueous suspension of *Alternaria solani* containing 0.2×10⁶ spores per ml. Then the trial plants were immediately transferred to a humid chamber. After 6 days at 20 to 23° C. and a relative humidity close to 100%, the extent of fungal attack on the leaves was visually assessed as % diseased leaf area.

In this trial, the plants which have been treated with 250 ppm of compounds I-3 and I-23, resp., showed an infection of not more than 7%, whereas the plants treated with 250 ppm of comparison compounds C and D, resp., were infected to at least 60%, and the untreated plants were infected to 100%.

In another trial, the plants which have been treated with 16 ppm of compound I-3 showed an infection of 15%, whereas the plants treated with 16 ppm of comparison compound E, were infected to 30%, and the untreated plants were infected to 90%.

Comparison Test 2: Control of Net Blotch on Barley Caused by *Pyrenophora teres*

The first fully developed leaves of pot grown barley of the variety "Igri" were sprayed to run-off with an aqueous suspension, containing the concentration of active ingredient or their mixture mentioned in the table below, prepared from a stock solution containing 10% of the active ingredient, 85% cyclohexanone and 5% emulsifier. The next day the treated plants were inoculated with an aqueous spore suspension of *Pyrenophora teres tritici* containing $0.02 \times 10^6$ spores/ml. Then the trial plants were immediately transferred to a humid chamber in the greenhouse. After 6 days of cultivation at 20 to 24° C. and a relative humidity close to 100%, the extent of fungal attack on the leaves was visually assessed as % diseased leaf area.

In this trial, the plants which have been treated with 250 ppm of compounds I-3 and I-23, resp., showed an infection of not more than 7%, whereas the plants treated with 250 ppm of comparison compounds C and D, resp., and the untreated plants were infected to 100%.

Comparison Trial 3: Fungicidal Control of Leaf Blotch on Wheat Caused by *Septoria tritici* (Protective)

Leaves of pot-grown wheat seedling of the variety "Riband" were sprayed to run-off with an aqueous suspension, containing the concentration of active ingredient as described below prepared from a stock solution containing 10% of the active ingredient, 85% cyclohexanone and 5% emulsifier. The plants were allowed to air-dry. At the following day the plants were inoculated with an aqueous spore suspension of Septoria tritici containing $2.0 \times 10^6$ spores/ml. Then the trial plants were immediately transferred to a humid chamber. After 2 weeks at 18 to 22° C. and a relative humidity close to 100% the extent of fungal attack on the leaves was visually assessed as % diseased leaf area.

In this trial, the plants which have been treated with 63 ppm of compounds I-3, I-5 and I-23, resp., showed no infection, whereas the plants treated with 63 ppm of comparison compounds B, C and D, resp., were infected from 20 to 60%, and the untreated plants were infected to 90%.

Comparison Test 4: Fungicidal Control of Rice Blast Caused by *Pyricularia oryzae* (Protective)

Leaves of pot-grown rice seedling of the variety "Tai-Nong 67" were sprayed to run-off with an aqueous suspension, containing the concentration of active ingredient as described below prepared from a stock solution containing 10% of the active ingredient, 85% cyclohexanone and 5% emulsifier. The plants were allowed to air-dry. At the following day the plants were inoculated with an aqueous spore suspension of *Pyricularia oryzae* containing $1.0 \times 10^6$ spores/ml. Then the trial plants were immediately transferred to a humid chamber. After 6 days at 22 to 24° C. and a relative humidity close to 100% the extent of fungal attack on the leaves was visually assessed as % diseased leaf area.

In this trial, the plants which have been treated with 250 ppm of compounds I-3, I-5, I-23, and I-63 resp., showed an infection of up to 30%, whereas the plants treated with 250 ppm of comparison compounds A, B, and E, resp., were infected from 60 to 80%, and the untreated plants were infected to 90 to 100%.

Comparison Test 5: Protective Control of Powdery Mildew on Cucumber

Cucumber seedlings of the variety "Chinesische Schlange" were grown in pots to the 2 leaf stage. The plants were then sprayed to run-off with an aqueous suspension, containing the concentration of active ingredient as described below, prepared from a stock solution containing 10% of the active ingredient, 85% cyclohexanone and 5% emulsifier. The next day the treated plants were inoculated with an aqueous spore suspension of cucumber powdery mildew (*Sphaerotheca fuliginea*). Then the trial plants were cultivated in a greenhouse at temperatures between 20 and 24° C. and a relative humidity between 60 and 80.%. After 8 days the extent of fungal attack on the leaves was visually assessed as % diseased leaf area.

In this trial, the plants which have been treated with 16 ppm of compound I-23 showed no infection, whereas the plants treated with 16 ppm of comparison compound E were infected to 90%, and the untreated plants were infected to 100%.

The invention claimed is:

1. 6-(2-Chloro-6-fluoro-phenyl)-triazolopyrimidines of formula I

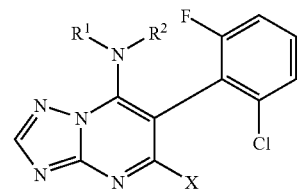

in which
  $R^1$ is straight-chain or branched $C_1$–$C_{10}$-alkyl, $C_3$–$C_8$-cycloalkyl, $C_5$–$C_9$-bicycloalkyl, $C_3$–$C_8$-cycloalkyl-$C_1$–$C_6$-alkyl, $C_1$–$C_{10}$-alkoxy-$C_1$–$C_6$-alkyl, $C_1$–$C_{10}$-haloalkyl, or is a phenyl group which is optionally substituted by one to three halogen atoms or $C_1$–$C_{10}$-alkyl or $C_1$–$C_{10}$-alkoxy groups,
  $R^2$ is hydrogen, $C_1$–$C_{10}$-alkyl or $C_1$–$C_{10}$-haloalkyl, and
  X is cyano, $C_1$–$C_6$-alkoxy, $C_1$–$C_6$-haloalkoxy or $C_3$–$C_8$-alkenyloxy.

2. Compounds of formula I according to claim 1 in which
  $R^1$ is branched $C_3$–$C_{10}$-alkyl, $C_3$–$C_8$-cycloalkyl, $C_5$–$C_9$-bicycloalkyl, $C_3$–$C_8$-cycloalkyl-$C_1$–$C_6$-alkyl, $C_1$–$C_{10}$-alkoxy-$C_1$–$C_6$-alkyl, $C_1$–$C_{10}$-haloalkyl, or is a phenyl group which is optionally substituted by one to three halogen atoms or $C_1$–$C_{10}$-alkyl or $C_1$–$C_{10}$-alkoxy groups,
  $R^2$ is hydrogen, $C_1$–$C_{10}$-alkyl or $C_1$–$C_{10}$-haloalkyl, and
  X is cyano, $C_1$–$C_6$-alkoxy, $C_1$–$C_6$-haloalkoxy or $C_3$–$C_8$-alkenyloxy.

3. Compounds of formula I according to claim 2 in which
  $R^1$ is branched $C_3$–$C_6$-alkyl, $C_1$–$C_6$-haloalkyl, $C_3$–$C_6$-cycloalkyl, or $C_5$–$C_9$-bicycloalkyl, and
  $R^2$ is hydrogen or $C_1$–$C_6$-alkyl.

4. Compounds according to claim 2 in which $R^2$ is hydrogen.

5. Compounds according to claim 2 in which X is methoxy.

6. Compounds according to claim 2 in which X is cyano.

7. Compounds of formula I according to claim 1, in which
  $R^1$ is straight chained or branched $C_1$–$C_6$-alkyl, $C_1$–$C_6$-haloalkyl, $C_3$–$C_6$-cycloalkyl, or $C_5$–$C_9$-bicycloalkyl, and
  $R^2$ is hydrogen or $C_1$–$C_6$-alkyl.

8. Compounds according to claim 1 in which $R^2$ is hydrogen.

9. Compounds according to claim 1 in which X is methoxy.

10. Compounds according to claim 1 in which X is cyano.

11. A composition suitable for controlling phytopathogenic fungi, comprising a solid or liquid carrier and a compound of the formula I as claimed in claim 1.

12. A method for controlling phytopathogenic fungi, which comprises treating the fungi or the materials, plants, the soil or the seed to be protected against fungal attack with an effective amount of a compound of the formula I as claimed in claim 1.

13. A process for the preparation of compounds of formula I as defined in claim 1 which comprises reacting 5-halogen-6-phenyl-triazolopyrimidines of formula II

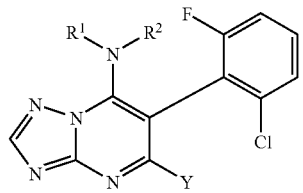

in which Y is halogen with a compound of formula III

M-X    III in which M is an ammonium-, tetraalkylammonium-, alkali metal- or alkaline earth metal cation and X is as defined in formula I to produce compounds of formula I.

* * * * *